US007688435B2

(12) United States Patent
Meeks

(10) Patent No.: US 7,688,435 B2
(45) Date of Patent: Mar. 30, 2010

(54) DETECTING AND CLASSIFYING SURFACE FEATURES OR DEFECTS BY CONTROLLING THE ANGLE OF THE ILLUMINATION PLANE OF INCIDENCE WITH RESPECT TO THE FEATURE OR DEFECT

(75) Inventor: Steven W. Meeks, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 653 days.

(21) Appl. No.: 11/485,798

(22) Filed: Jul. 13, 2006

(65) Prior Publication Data

US 2006/0250612 A1 Nov. 9, 2006

Related U.S. Application Data

(63) Continuation-in-part of application No. 11/269,336, filed on Nov. 8, 2005, now Pat. No. 7,218,391, which is a continuation of application No. 10/444,652, filed on May 22, 2003, now Pat. No. 7,123,357, which is a continuation-in-part of application No. 10/219,632, filed on Aug. 14, 2002, now Pat. No. 6,909,500, which is a continuation-in-part of application No. 10/126,154, filed on Apr. 19, 2002, now Pat. No. 6,930,765, which is a continuation-in-part of application No. 10/029,957, filed on Dec. 21, 2001, now Pat. No. 6,897,957, which is a continuation-in-part of application No. 09/861,280, filed on May 18, 2001, now Pat. No. 6,757,056, which is a continuation of application No. 09/818,199, filed on Mar. 26, 2001, now abandoned, which is a continuation-in-part of application No. 09/718,054, filed on Nov. 20, 2000, now Pat. No. 6,392,749, which is a continuation-in-part of application No. 09/414,388, filed on Oct. 7, 1999, now Pat. No. 6,665,078, which is a continuation-in-part of application No. 09/347,622, filed on Jul. 2, 1999, now Pat. No. 6,717,671, which is a continuation-in-part of application No. 09/136,897, filed on Aug. 19, 1998, now Pat. No. 6,031,615.

(60) Provisional application No. 60/059,740, filed on Sep. 22, 1997.

(51) Int. Cl.
*G01N 21/00* (2006.01)

(52) U.S. Cl. .............................. 356/237.2; 250/559.14; 250/559.42; 250/559.45; 356/237.1; 356/239.8

(58) Field of Classification Search ............ 250/559.14, 250/559.42–559.45; 356/237.1–237.6, 239.3–239.8
See application file for complete search history.

(56) References Cited

U.S. PATENT DOCUMENTS 2,593,189 A 4/1952 Rinia (Continued)

FOREIGN PATENT DOCUMENTS

DE 4105192 8/1991

(Continued)

*Primary Examiner*—Gregory J Toatley, Jr.
*Assistant Examiner*—Iyabo S Alli
(74) *Attorney, Agent, or Firm*—Luedeka, Neely & Graham, P.C.

(57) ABSTRACT

Scratches, pits and particles which are smaller or larger than the beam size may be measured and identified by a single and dual multiple beam techniques. In one embodiment, this the invention uses a pair of orthogonally oriented white light beams, one in the radial and one in the circumferential direction. The scattered light from the radial and circumferential beams allows the detection and classification of particles, pits and scratches. In other embodiments, single beam techniques are used to classify radial and circumferential defects.

28 Claims, 12 Drawing Sheets

U.S. PATENT DOCUMENTS

| | | |
|---|---|---|
| 4,378,159 A | 3/1983 | Galbraith |
| 4,585,348 A | 4/1986 | Chastang |
| 4,601,575 A | 7/1986 | Tamaki |
| 4,650,333 A | 3/1987 | Crabb |
| 4,794,264 A | 12/1988 | Quackenbos et al. |
| 4,870,631 A | 9/1989 | Stoddard |
| 4,873,430 A | 10/1989 | Juliana |
| 4,905,311 A | 2/1990 | Hino et al. |
| 4,999,510 A | 3/1991 | Hayano |
| 5,017,012 A | 5/1991 | Merritt, Jr. et al. |
| 5,026,982 A * | 6/1991 | Stroman .................. 250/221 |
| 5,067,817 A | 11/1991 | Glenn |
| 5,125,741 A | 6/1992 | Okada |
| 5,168,386 A | 12/1992 | Galbraith |
| 5,189,481 A * | 2/1993 | Jann et al. ............... 356/237.2 |
| 5,270,794 A | 12/1993 | Tsuji |
| 5,392,116 A | 2/1995 | Makosch |
| 5,416,594 A * | 5/1995 | Gross et al. ............. 356/237.5 |
| 5,565,979 A | 10/1996 | Gross |
| 5,604,585 A | 2/1997 | Johnson et al. |
| 5,608,527 A | 3/1997 | Valliant et al. |
| 5,610,897 A | 3/1997 | Yamamoto |
| 5,633,747 A | 5/1997 | Nikoonahad |
| 5,644,562 A | 7/1997 | de Groot |
| 5,737,085 A | 4/1998 | Zollars et al. |
| 5,798,829 A | 8/1998 | Vaez-Iravani |
| 5,864,394 A | 1/1999 | Jordan, III et al. |
| 5,880,838 A | 3/1999 | Marx et al. |
| 5,883,714 A | 3/1999 | Jann et al. |
| 5,898,500 A | 4/1999 | Canteloup et al. |
| 5,903,342 A | 5/1999 | Yatsugake |
| 5,963,314 A | 10/1999 | Worster et al. |
| 5,985,680 A | 11/1999 | Singhal |
| 5,986,763 A | 11/1999 | Inoue |
| 5,995,226 A | 11/1999 | Abe |
| 6,020,966 A | 2/2000 | Ausschnitt et al. |
| 6,031,615 A | 2/2000 | Meeks |
| 6,081,325 A | 6/2000 | Leslie |
| 6,091,493 A | 7/2000 | Stover et al. |
| 6,122,046 A | 9/2000 | Almogy |
| 6,130,749 A | 10/2000 | Meeks |
| 6,154,280 A | 11/2000 | Borden |
| 6,169,601 B1 | 1/2001 | Eremin et al. |
| 6,172,752 B1 | 1/2001 | Haruna et al. |
| 6,198,533 B1 | 3/2001 | Meeks |
| 6,229,610 B1 | 5/2001 | Meeks |
| 6,268,919 B1 | 7/2001 | Meeks |
| 6,392,749 B1 | 5/2002 | Meeks |
| 6,433,877 B2 | 8/2002 | Watanabe et al. |
| 6,515,745 B2 | 2/2003 | Vurens et al. |
| 6,556,290 B2 | 4/2003 | Maeda et al. |
| 6,603,541 B2 | 8/2003 | Lange |
| 6,617,603 B2 | 9/2003 | Ishiguro et al. |
| 6,624,884 B1 | 9/2003 | Imaino |
| 6,624,894 B2 | 9/2003 | Olszak et al. |
| 6,665,078 B1 | 12/2003 | Meeks |
| 6,678,046 B2 | 1/2004 | Opsal |
| 6,687,008 B1 | 2/2004 | Peale |
| 6,690,473 B1 | 2/2004 | Stanke et al. |
| 6,704,435 B1 | 3/2004 | Imaino |
| 6,717,671 B1 | 4/2004 | Meeks |
| 6,751,044 B1 | 6/2004 | Meeks |
| 6,757,056 B1 | 6/2004 | Meeks et al. |
| 6,781,103 B1 | 8/2004 | Lane |
| 6,804,003 B1 | 10/2004 | Wang et al. |
| 6,813,034 B2 | 11/2004 | Rosencwaig et al. |
| 6,917,433 B2 | 7/2005 | Levy et al. |
| 6,940,609 B2 | 9/2005 | Scheiner |
| 6,956,660 B2 | 10/2005 | Meeks et al. |
| 7,019,850 B2 | 3/2006 | Finarov |
| 7,023,547 B2 | 4/2006 | Venkatasubbarao et al. |
| 7,042,556 B1 | 5/2006 | Sun |
| 7,042,577 B1 | 5/2006 | Jacob et al. |
| 7,046,352 B1 | 5/2006 | Dayal et al. |
| 7,075,630 B2 | 7/2006 | Meeks |
| 7,113,284 B1 | 9/2006 | Meeks |
| 7,161,683 B2 | 1/2007 | Weitzel |
| 2002/0015146 A1 | 2/2002 | Meeks |
| 2002/0107650 A1 | 8/2002 | Wack et al. |
| 2002/0118359 A1 | 8/2002 | Fairley |
| 2002/0145740 A1 | 10/2002 | Meeks |
| 2002/0163634 A1 | 11/2002 | Meeks |
| 2003/0025905 A1 | 2/2003 | Meeks |
| 2003/0179370 A1 | 9/2003 | Goldberg et al. |
| 2004/0017561 A1 | 1/2004 | Meeks |
| 2004/0046959 A1 | 3/2004 | Meeks |
| 2004/0130710 A1 | 7/2004 | Hwang et al. |
| 2004/0160604 A1 | 8/2004 | Meeks |
| 2004/0169850 A1 | 9/2004 | Meeks |
| 2004/0233419 A1 | 11/2004 | Meeks |
| 2005/0023491 A1 | 2/2005 | Young |
| 2005/0057747 A1 | 3/2005 | Meeks |
| 2005/0206888 A1 | 9/2005 | Yoshida et al. |
| 2006/0072106 A1 | 4/2006 | Matsui et al. |
| 2007/0030493 A1 | 2/2007 | Zettler et al. |

FOREIGN PATENT DOCUMENTS

| | | |
|---|---|---|
| EP | 0080540 | 6/1983 |
| JP | 03085514 | 4/1991 |
| JP | 07055702 | 3/1995 |
| JP | 10325711 | 12/1998 |
| WO | WO9416310 | 7/1994 |

* cited by examiner

DETECTING AND CLASSIFYING SURFACE FEATURES OR DEFECTS BY CONTROLLING THE ANGLE OF THE ILLUMINATION PLANE OF INCIDENCE WITH RESPECT TO THE FEATURE OR DEFECT

RELATED APPLICATIONS

This application is a continuation-in-part of U.S. patent application Ser. No. 11/269,336, filed Nov. 8, 2005, now U.S. Pat. No. 7,218,391 entitled Material Independent Optical Profilometer, which is a continuation of U.S. patent application Ser. No. 10/444,652, entitled Method of Detecting and Classifying Scratches and Particles on Thin Film Disks or Wafers, by Steven W. Meeks, filed May 22, 2003, now U.S. Pat. No. 7,123,357 which is a continuation-in-part of U.S. patent application Ser. No. 10/219,632 filed on Aug. 14, 2002, (U.S. Pat. No. 6,909,500) which is a continuation-in-part of U.S. patent application Ser. No. 10/126,154 filed on Apr. 19, 2002, (U.S. Pat. No. 6,930,765) which is a continuation-in-part of U.S. patent application Ser. No. 10/029,957 filed on Dec. 21, 2001, (U.S. Pat. No. 6,897,957) which is a continuation-in-part of U.S. patent application Ser. No. 09/861,280 (U.S. Pat. No. 6,757,056) filed on May 18, 2001, which is a continuation of U.S. patent application Ser. No. 09/818,199 filed on Mar. 26, 2001, now abandoned which is a continuation-in-part of U.S. patent application Ser. No. 09/718,054 filed on Nov. 20, 2000 (U.S. Pat. No. 6,392,749), which is a continuation-in-part of U.S. patent application Ser. No. 09/414,388 filed on 7 Oct. 1999 (U.S. Pat. No. 6,665,078), which is a continuation-in-part of U.S. patent application Ser. No. 09/347,622 filed on 2 Jul. 1999 (U.S. Pat. No. 6,717,671), which is a continuation-in-part of U.S. patent application Ser. No. 09/136,897 filed on Aug. 19, 1998 (U.S. Pat. No. 6,031,615), which claims priority from provisional application No. 60/059,740 filed on 22 Sep. 1997 (applicant's reference number 2924), which are all incorporated by reference herein in their entirety.

BACKGROUND OF THE INVENTION

I. Field of the Invention

The present invention is directed toward detecting defects on substrates such as transparent and coated glass substrates, silicon wafers, and magnetic disk media and more particularly toward measuring wear, surface roughness, scratches, particles, stains, pits, mounds, surface topography, step heights, and inclusions by shining bright light along a direction on the surface of the substrate.

II. Description of Background Art

Coated thin film disks are used in a variety of industries including the semiconductor and the magnetic hard disk industry. A computer hard disk (magnetic storage device) is a non-volatile memory device that can store large amounts of data. One problem that the manufacturers of hard disks experience is how to maximize the operating life of a hard disk. When a hard disk fails the data stored therein may be difficult, expensive, or impossible to retrieve. Failure of a hard disk may be caused by defects on the surface of the thin film disk. It is important to be able to detect and classify these defects in order to prevent disk drive failure and to control the manufacturing process.

A schematic of a thin film disk used in magnetic storage devices is shown in FIG. 1. It includes a magnetic thin film (layer) 106, which is deposited upon a substrate 108 (typically a NiP plated Al—Mg alloy or glass). The magnetic thin film 106 can be protected by a thin film of carbon 104 (carbon layer), for example, whose thickness is typically 20 to 200 Angstroms (Å). The carbon layer 104 is typically coated with a thin layer (10 to 30 Angstroms) of a fluorocarbon lubricant 102 (lubricant layer). The lubricant layer 102 serves to increase the durability of the underlying carbon layer 104 particularly when the magnetic read/write head contacts the disk, for example when the disk drive is turned off. The hard disk drive industry has been dramatically improving storage capacity by flying the thin film head closer to the surface of the thin film disk. As a result even very small defects can cause a hard drive to fail. These defects may be topographic such as scratches, pits, mounds, or particles or they may be non-topographic such as stains or inclusions. It is useful to measure all these types of defects to control the disk manufacturing process and improve disk drive manufacturing yield.

A schematic of a semiconductor wafer is shown in FIG. 2. The structure of a semiconductor wafer can be very complex and FIG. 2 shows only a typical structure of a wafer that is undergoing the copper dual damascene process. In FIG. 2, 201 is the copper layer 202 is the second plasma enhanced chemical vapor deposited (PECVD) oxide layer, 203 is the first PECVD oxide layer and 204 is the silicon substrate. The copper layer 201 is polished down using a chemical mechanical polishing (CMP) process until only the via holes and copper lines remain. The problem is that the CMP process can leave residual copper, nitride, or CMP slurry on the surface of the wafer. In addition, stains, particles, scratches, and microwaviness may be present on the polished wafer. It is useful to detect and measure such defects to control the process of making the wafer. Fewer defects will also mean greater wafer yields at the end of the process. The problem in the hard disk, semiconductor and photonics industries is to inspect these magnetic disks and wafers for defects such as particles, scratches, pits, mounds, stains, topographic irregularities and inclusions. Conventional techniques to solve these problems are discussed in U.S. Pat. No. 4,674,875, 5,694,214, 5,748,305, and 6,157,444 that are all incorporated by reference herein in their entirety. These patents describe techniques to measure defects using essentially sophisticated scatterometers and reflectometers. Prior art systems also measure defects by shining white light on a surface at a high angle of incidence; the image of the surface is then captured with a charge couple device (CCD) camera and analyzed for defects. None of these systems enables the detection and classification of surface features or defects by controlling the angle of the illumination plane of incidence with respect to the features or defects in order to detect and differentiate topological and non-topological defects.

Thus, what is needed is a system and method for examining the surface of substrates, such as silicon wafers or magnetic disk media, for topological and non-topological defects and features by controlling the angle of illumination plane of incidence with respect to the features or defects.

SUMMARY

A system and method are provided for categorizing defects, such as scratches, particles, and pits, on the surface of an object. The method optimally detects particles, circumferential and radial scratches, by controlling the angle of the illumination plane of incidence with respect to the feature or defect on the surface of an object. The scrattered light intensities produced when the light beams strike a defect are measured by a CCD camera the scattered light intensities of the beams are compared to determine the aspect ratio of the defect.

DETAILED DESCRIPTION

A preferred embodiment of the present invention is now described with reference to the figures where like reference numbers indicate identical or functionally similar elements. Also in the figures, the left most digit of each reference number corresponds to the figure in which the reference number is first used.

One method of detecting particles or defects on substrates such as silicon wafers or magnetic disk media is to shine bright light on the surface of the substrate. The light scattered by particles or defects can then be detected by imaging optics and detectors such as CCD cameras.

It is also desirable to be able to differentiate the type of defects detected. For example, when inspecting textured magnetic disk media, knowing if the scattered light signal from a position on the substrate is from the surface texture or a particle is desirable. This type of information will help the user to pinpoint the source of the defect.

U.S. patent application Ser. No. 10/444,652 filed on May 22, 2003, which is incorporated by reference herein in its entirety, discloses a system and method for detecting defects on the surface of an object by using a pair of substantially orthogonal directed laser beams, one in the radial and one in the circumferential direction. It also discloses single beam techniques to classify radial and circumferential defects.

Figure 1:
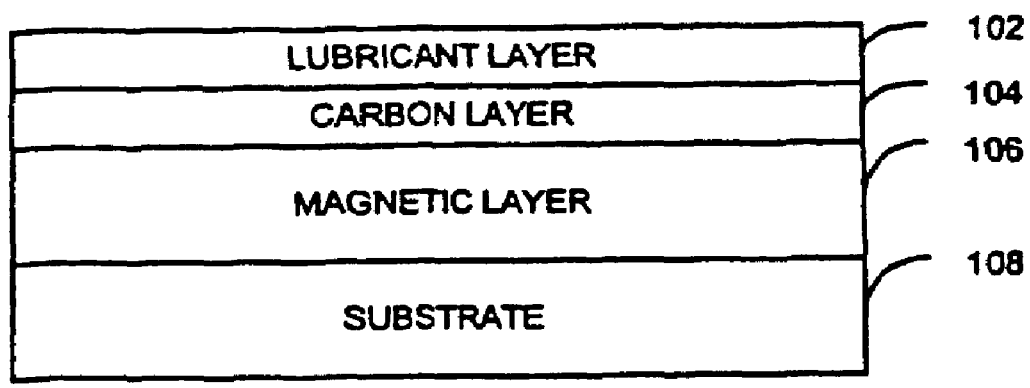
FIG. 1 is an illustration of a thin film.
Figure 2:
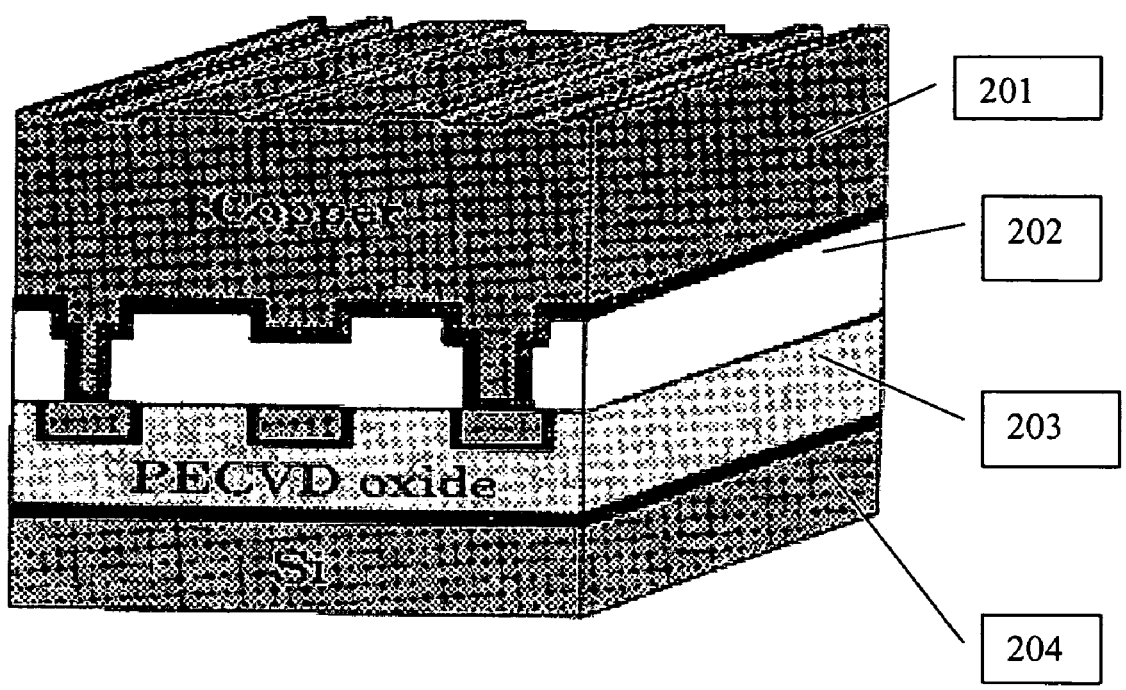
FIG. 2 is an illustration of a semiconductor wafer that can be measured with one embodiment of the present invention.
Figure 3:
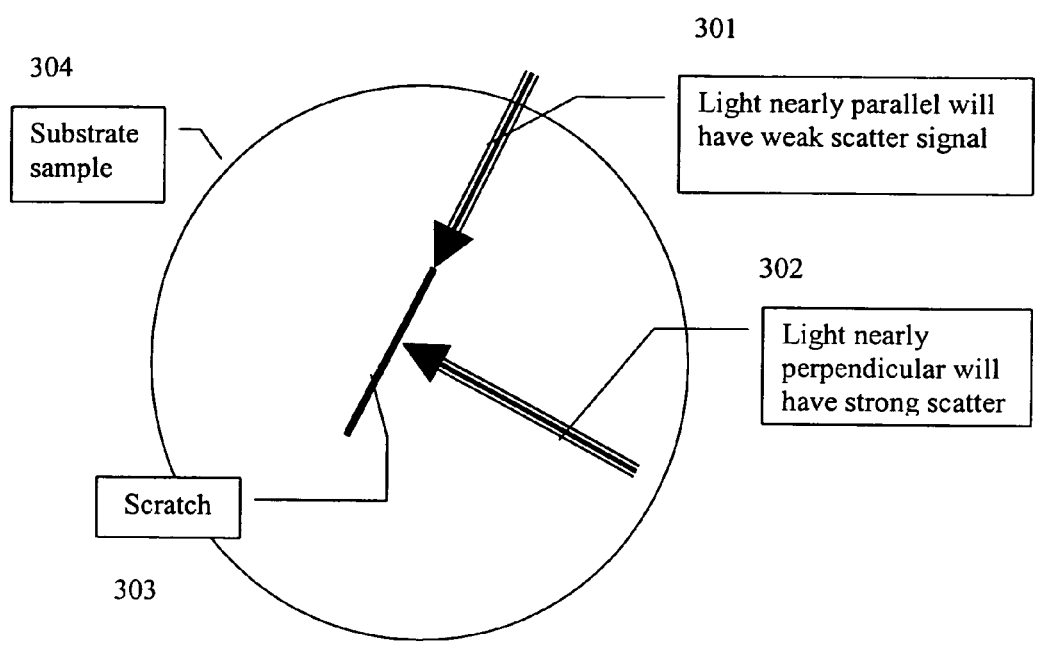
FIG. 3 is an illustration of two different angles of the illumination plane of incident with respect to the defect.

FIG. 3 illustrates the scattering of light from an anisotropic defect by varying with the angle of the illumination plane of incidence with respect to the defect. When light is directed towards a surface the amount of light scattered by anisotropic defects such as a scratch 303 depends on the angle between the scratch itself and the plane of incidence of the light source. A light beam 302 whose plane of incidence is nearly perpendicular (as viewed from above the surface) to the scratch line scatters more light than a beam 301 with a plane of incidence that is nearly parallel to the scratch. By contrast, a particle, which is substantially isotropic in shape, will generate scatter from both the radial and circumferential light beam; that is, the amount of light scattered is less dependent on the plane of illumination.

Figure 4A:
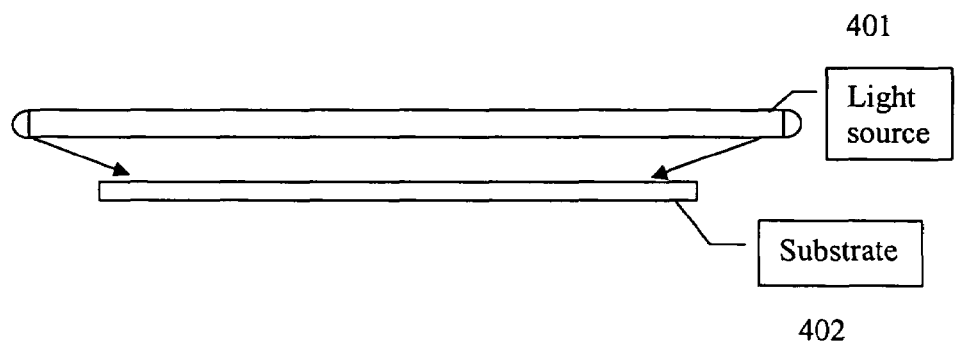
FIG. 4A is an illustration of a side view of a light source being directed across a substrate.

The scratch or texture can be a straight line or a circumferential line (circular). On magnetic disk media, typically the texture line is circumferential (nearly concentric to the disk itself). FIG. 4A shows a side view of a light source 401 being directed across a substrate 402. To obtain a strong scatter signal from these texture line the light beam can be directed from the edge of the disk/substrate 402 toward the center of the disk/substrate 402 (the radial direction).

Figure 4B:
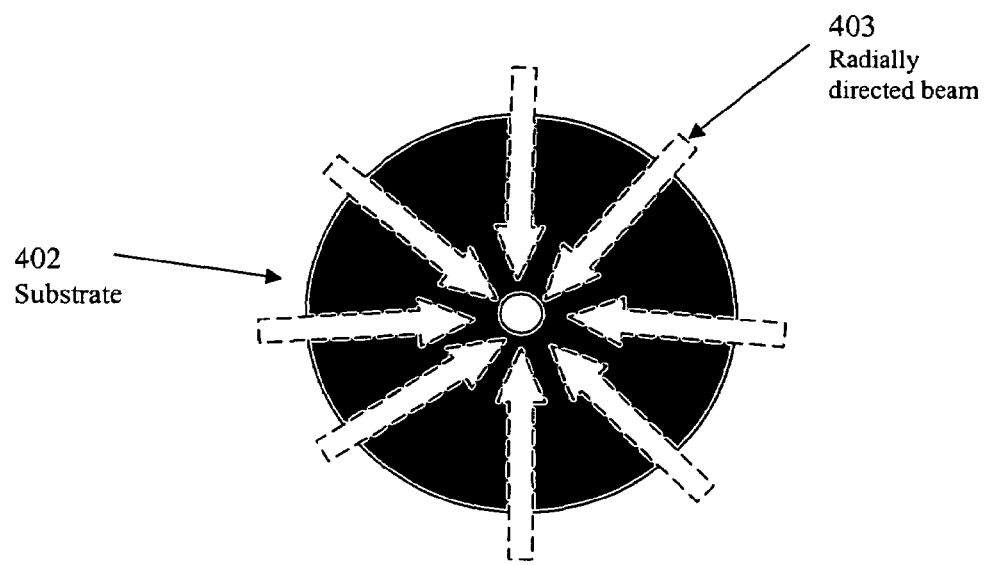
FIG. 4B is an illustration of light beams directed radially across a disk.

One method of directing the light beam along radial directions toward the center of the disk 402 is to use a series of beams, e.g., eight beams, which approximate radial illumination on the disk. In other embodiments, more or less beams may be used to cover the surface of the disk. FIG. 4B shows eight beams directed radially toward the center of disk 402. Using this technique, it is not necessary to rotate the disk, only to image it with optics and a CCD camera. This can be done by illuminating with all beams simultaneously or sequentially.

Figure 5:
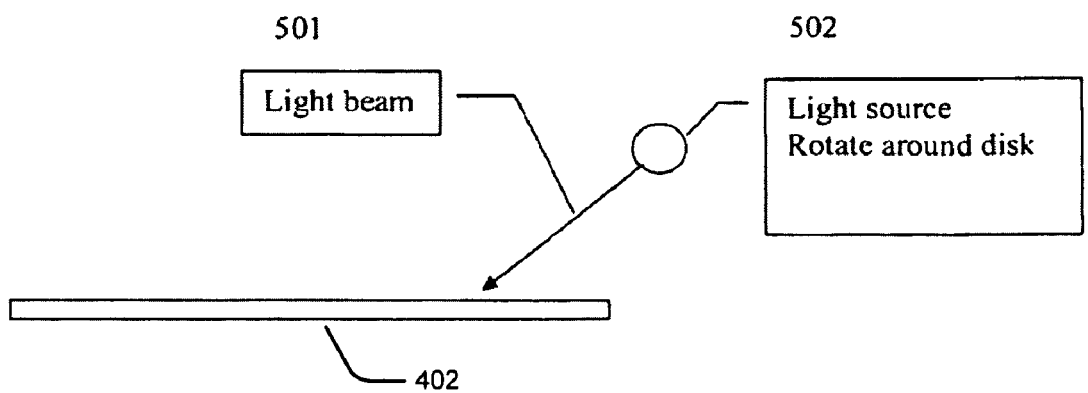
FIG. 5 is an illustration of a method to direct a light source along a radial direction.

Another method, as illustrated in FIG. 5, is to rotate the disk with respect to the light source 502 or rotate the light source 502 around the disk. The light source is rotated and multiple CCD images are obtained while the light source is in the process of rotation. The process of rotating the light source and obtaining a CCD image are synchronized so that every point on the surface of the wafer or disk is imaged with the CCD while it is being illuminated by the rotating light source.

Figure 6:
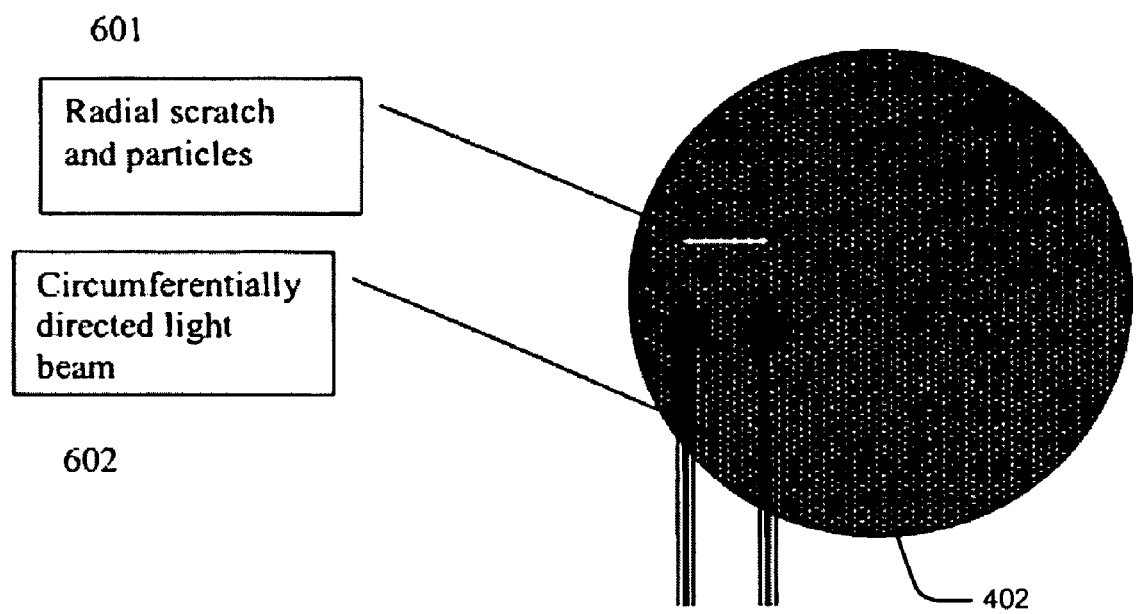
FIG. 6 is an illustration of directing light along a circumferential direction.

A CCD camera or another type of detector is placed above the disk to collect the scattered light. The above described illumination technique will preferentially detect scratches which are oriented in the circumferential direction. In order to detect particles or radial scratches it is desired to minimize the signal from the circumferential texture. This may be accomplished by directing the light in the circumferential direction as shown in FIG. 6.

The circumferentially oriented beam 602 will produce only minimal scatter from the circumferential texture and as a result much smaller particles may be detected with a circumferentially oriented beam since the "noise" from the texture is not present. The circumferentially oriented beam will also optimally detect radial scratches and particles 601. One way to obtain the circumferential illumination is shown in FIG. 6. In this case, the disk must be rotated to inspect the entire surface. Another means of producing a circumferential illumination is shown in FIG. 7.

Figure 7:
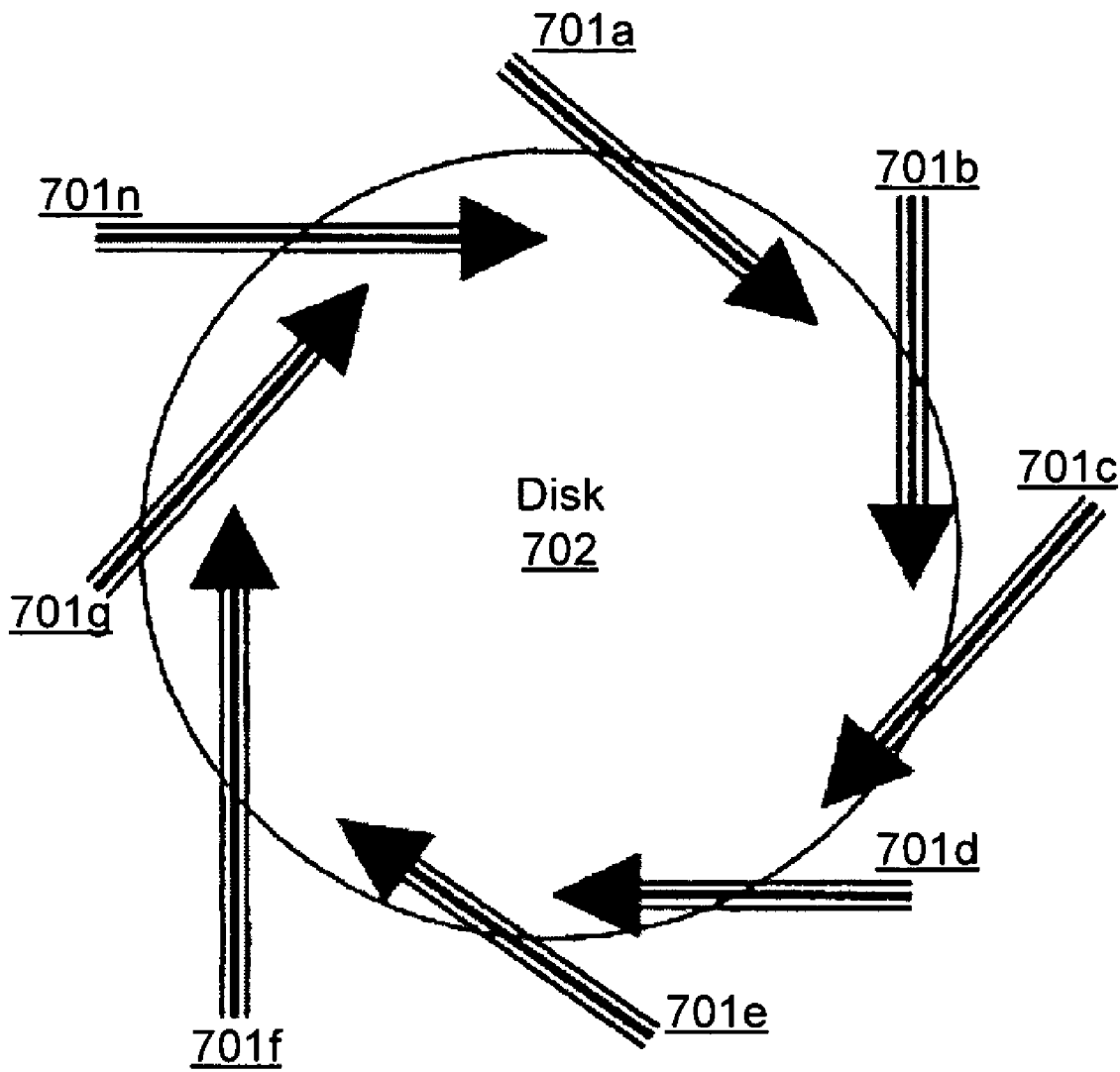
FIG. 7 illustrates a method of directing light along circumferential directions to produce an approximate tangential illumination on a disk.

In FIG. 7, a series of eight beams 701a, 701b, 701c, 701d, 701e, 701f, 701g, 701n is shown which produces an approximate tangential illumination on the disk 702. More or less beams may be used to cover the surface of the disk 702. In this case, it is not necessary to rotate the disk 702, only to image it with optics and a CCD camera.

Figure 8:
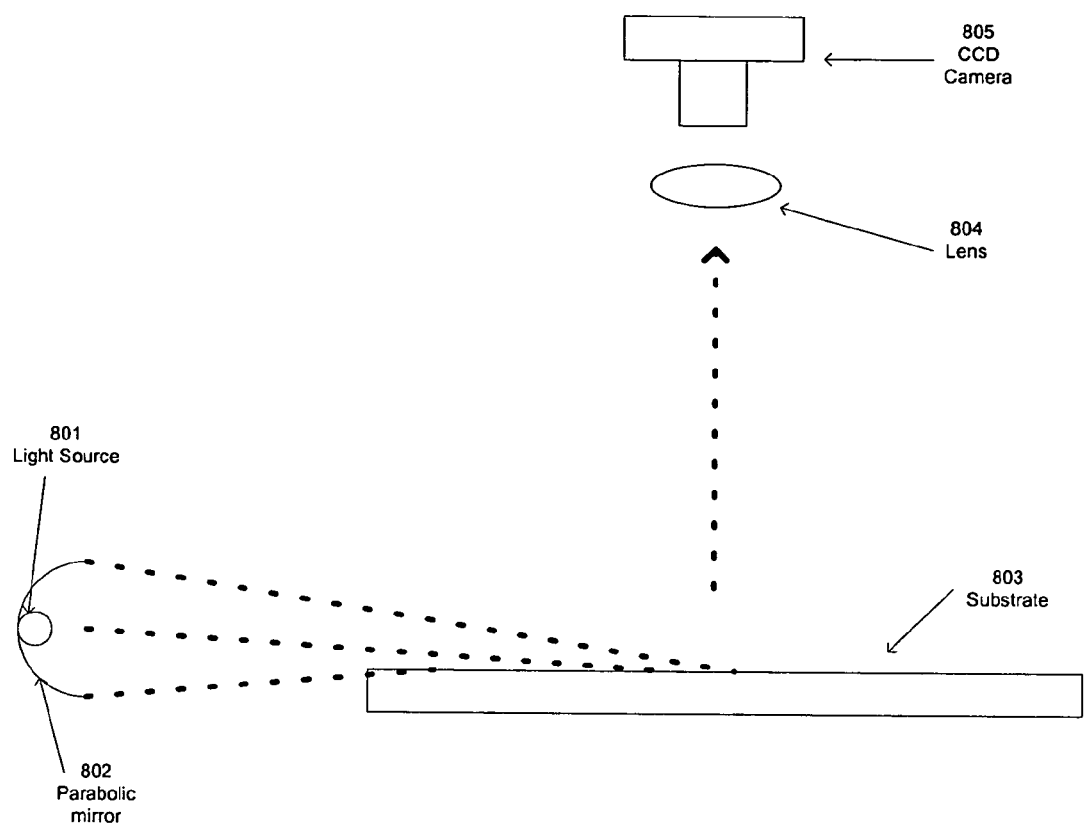
FIG. 8 is an illustration of an optical setup for an apparatus to detect defects using white light and a CCD camera.

FIG. 8 illustrates an embodiment of the present invention. White or colored light is directed onto the surface of a substrate from a source 801. The light source 804 can be any source that is capable of producing white or colored light, including tungsten, incandescent or halogen lamp. In the preferred embodiment, a halogen lamp is used as the white or colored light source. Parabolic mirror 802 directs the light rays as quasi-collimated light beams onto the surface of substrate 803. In one embodiment, the beam is directed along a radial direction at a high angle of incidence in order to measure circumferential defects. In another embodiment, the beam is directed along a circumferential direction at a high angle of incidence in order to measure radial defects.

The light intensity from the surface of the substrate scatters up to Fresnel lens 804, which focuses the beams onto a high resolution CCD camera 805. CCD camera 805 captures the image from the scattered light. The CCD camera images the surface feature from the scattered light into pixels on the CCD array. The pixel data from the CCD array is digitized and read by a computer. In an embodiment of the above-described functions and features for classifying defects, a computing device with a central processing unit (CPU) is used to process the scattered light image data collected from the disk surface. The CPU executes an algorithm to process the images in order to compare and classify the defects. For example, the algorithm can be implemented as a computer program stored on a conventional storage device, in firmware or in hardware.

Figure 9:
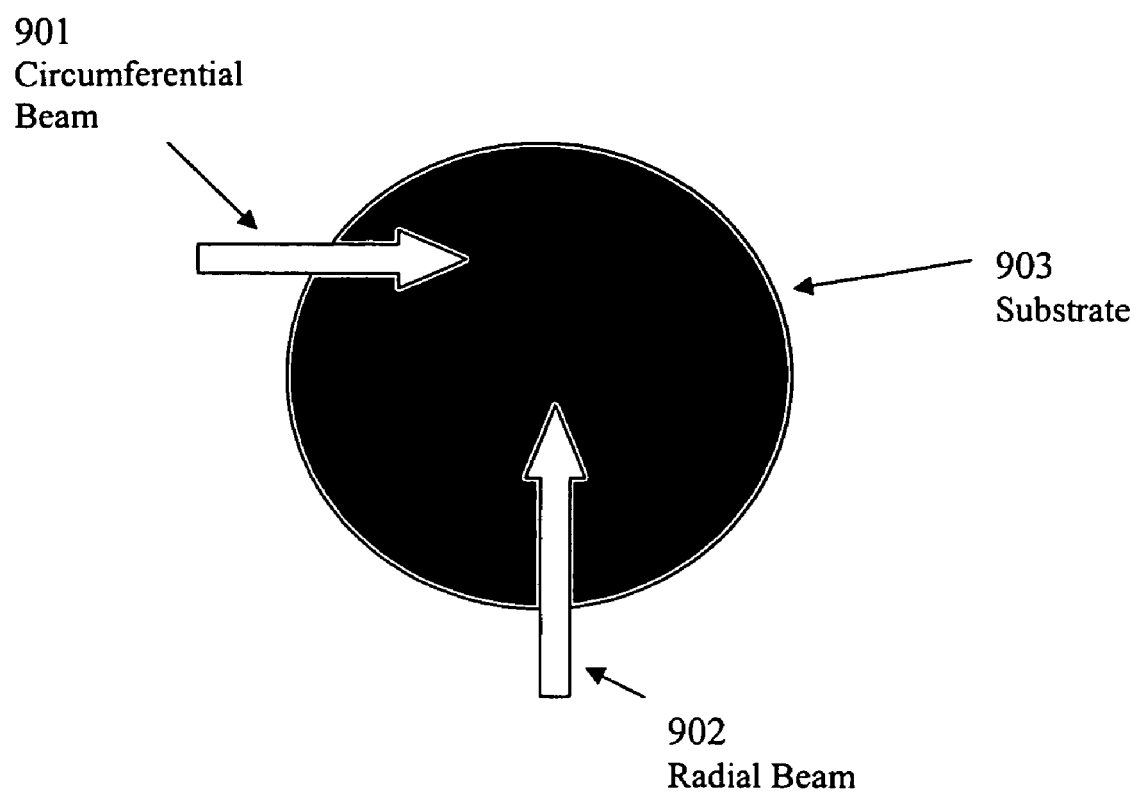
FIG. 9 illustrates an embodiment with a circumferentially directed beam and a radially directed beam.
Figure 10:
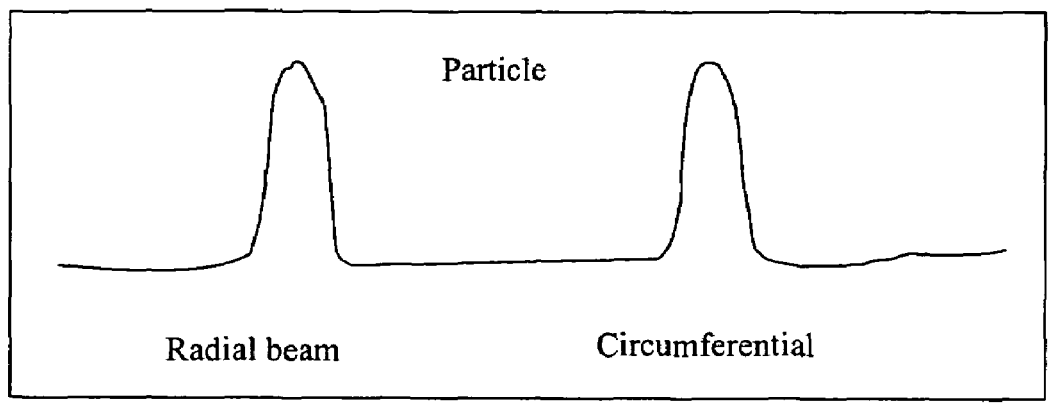
FIG. 10 is an illustration of the scattered light detection of a particle, pit, and scratch from both the radial and circumferential beams.
Figure 10:
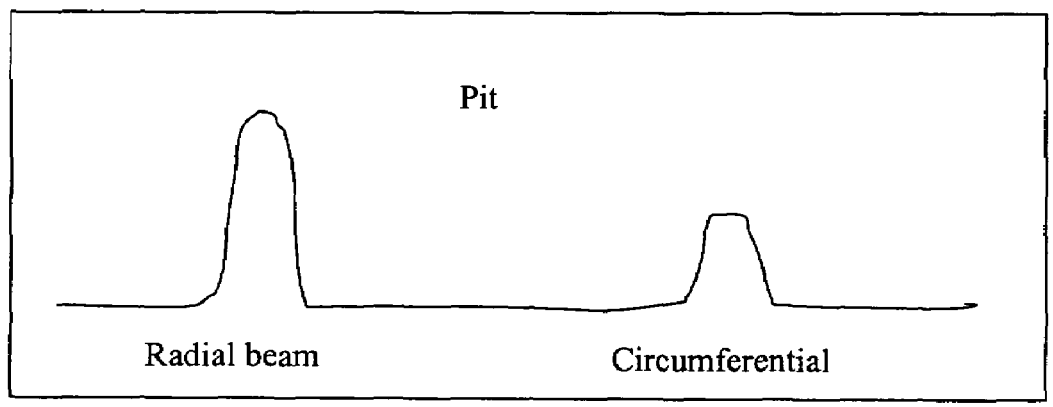
Figure 10:
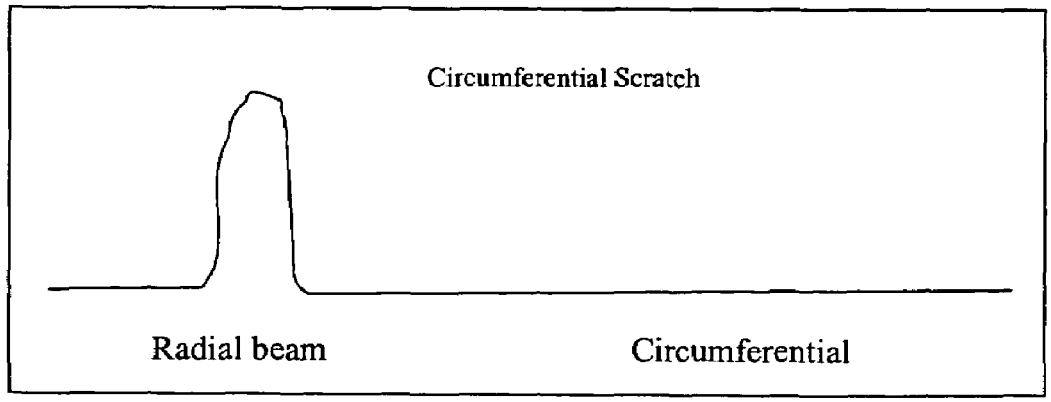

The optical device shown in FIG. 8 can be arranged so that there are two identical sets of light sources with quasi-collimated white or colored light beams in orthogonal planes of incidence. In an embodiment, the plane of incidence of light beam one 901 is in the circumferential direction and the plane of incidence of light beam two 902 is in the radial direction as shown in FIG. 9. Alternatively, light beam one 901 can be a set of circumferentially orient beams as illustrated in FIG. 7 and described above, and light beam two 902 can be a set of radially oriented beams as illustrated in FIG. 4B and described above. In such an embodiment, it would not be necessary to rotate the disk, only to image it with optics and a CCD camera. The CCD camera 805 (in FIG. 8) will receive scattered light from both circumferential and radial beams, one directional set at a time. The two beams (or sets of beams) can be detected in sequential order—e.g., circumferential beams followed by radial beams, or vice versa. The data may also be taken in parallel, that is, both radial and circumferential beams are on at the same time, although this will result in reduced particle sensitivity. Scratches which are oriented perpendicular to the plane of incidence of the light will generate a strong scatter signal, while those oriented parallel to the plane of incidence will generate substantially no scattered signal. For example, a circumferentially oriented scratch will generate a strong scatter signal when the radial beam (light beam 902 in FIG. 9) crosses it and substantially no scatter when the circumferential beam (light beam 901 in FIG. 9) crosses it. By contrast, a particle which is substantially isotropic in shape will generate scatter from both the radial and circumferential light beams. Since a small particle is substantially isotropic, it will scatter substantially equally when illuminated by the radial or circumferential beam. In the case of a substantially isotropic particle the signals from both beams are substantially equal. In the case of a circumferentially oriented scratch, the radial beam gives a strong signal and the circumferential beam gives substantially no signal. This is because the scratch is strongly anisotropic in its scattering characteristics. That is, a beam whose plane of incidence is oriented perpendicular to the long direction of the scratch scatters much more than a beam whose plane of incidence is parallel to the long direction of the scratch. The ratio of the scattered amplitudes of the scatter light from the radial and circumferential beams will discriminate a pit from a scratch or particle. This is illustrated in FIG. 10 which shows at the top the relative amplitudes of the scattered light of the particle in the radial and circumferential beams. In this case the amplitudes are substantially equal. The middle picture in FIG. 10 shows the amplitudes for a small oval shaped pit. The amplitudes are not equal. The bottom picture in FIG. 10 shows the amplitudes for a circumferentially oriented scratch. In this case the scatter signal comes substantially only from the radial beam. If the scratch were oriented in the radial direction the scatter signal would come substantially from the circumferential beam and substantially none from the radial beam. If the scratch were oriented at 45° to the radial direction then the scattered signal would be equal from both the radial and circumferential beams. It is also possible to orient the planes of the light beams at angles other than 90°. In another embodiment, the orthogonal pair of beams may be oriented at an angle to the radial and circumferential directions. In this manner, one may more easily detect scratches, which lie at directions which are neither radial nor circumferential.

In an embodiment, the apparatus to detect scratches and particles is that shown in FIG. 8. The CCD Camera 805 detects the scatter light image collected from each radius and angle on the disk surface. This data is processed by denoting excursions (above or below) of the data from the local average. The local average is determined by averaging the data for a specified length along a specified orientation such as the radial or circumferential direction. The local average is moved throughout the entire data set and each pixel is compared to the local average. Points, which exceed the specified threshold above or below the local average, are denoted as defects. All the points, which exceed the specified threshold, are put together in a map of the surface showing the locations and amplitude of all the defects. Contiguous or substantially contiguous points on the defect map are classified as a single defect. The amplitude of the scattered light from the radial and the circumferential beams are then compared to determine if the defect is a scratch, particle or pit.

In an embodiment of the above-described functions and features for comparing and classifying defects, a computing device with a central processing unit (CPU) is used to process the scattered lighter image data collected from the disk surface. The CPU executes the above-described algorithm to process the images in order to compare and classify the defects. For example, the algorithm can be implemented as a computer program stored on a conventional storage device, in firmware or in hardware.

Figure 11:
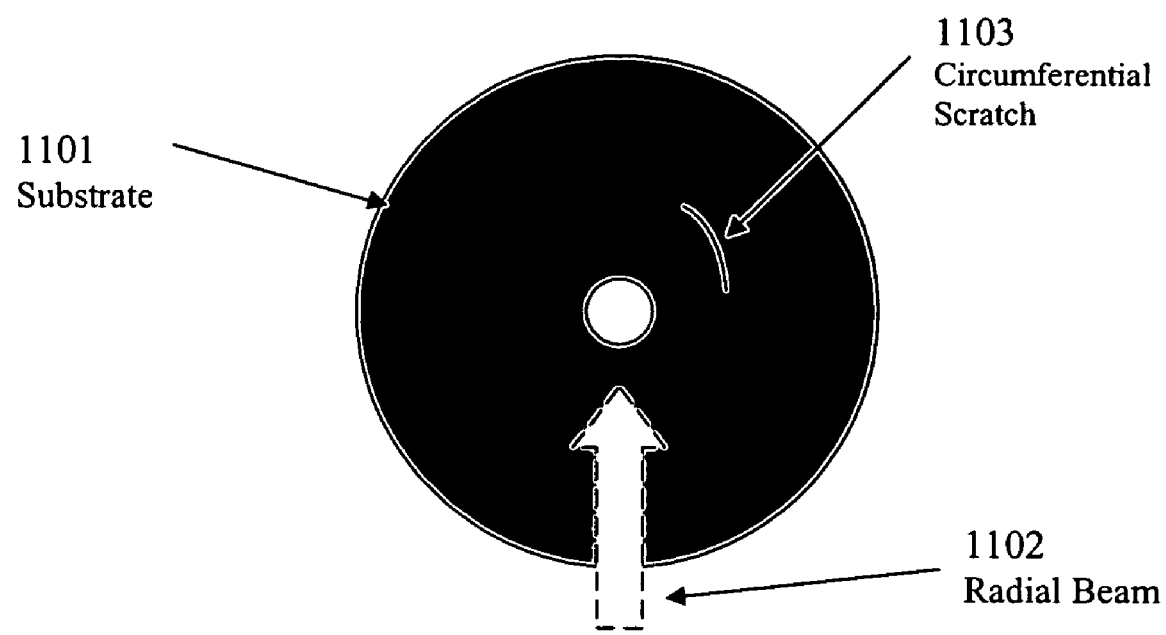
FIG. 11 is an illustration of a radial beam used for detecting circumferential scratches.

The above embodiments have described optical designs that compare a radial and a circumferentially oriented light beams to determine if a defect is a scratch or a particle. It is also possible to detect and classify a defect as a scratch or a particle by using only a single light beam or a set of light beams oriented in either the radial or circumferential directions. The case of detecting circumferential scratches is shown in FIG. 11. This is accomplished by orienting the plane of incidence of the light source shown in FIG. 8 in the radial direction as indicated by 1102. Alternatively, a set of beams oriented in the radial directions as illustrated in FIG. 4B can be used, in which case it would not be necessary to rotate the disk. In this manner, the circumferential texture scratches 1103 on disk or wafer 1101 will have the maximum amount of scattered light. The amount of scatter from the circumferential texture is typically so great that only large particles may be detected. As a result, much of the information detected by the embodiment described by FIG. 11 is from the circumferential texture. The texture defects are noted by excursions in scattered amplitude that are significantly above the background. The texture defects are separated from the signal for large particles by using an algorithm that measures the aspect ratio of the detected defect. A texture scratch will have a long and thin aspect ratio and a large particle will not.

In an embodiment, the apparatus to detect circumferential scratches and particles is that shown in FIG. 8 with the optical plane of incidence oriented in the radial direction. CCD camera 805 detects the scattered light image from each radius and angle on the disk surface. This data is processed by denoting excursions (above or below) of the data from the local average. The local average is determined by averaging the data for a specified length along a specified orientation such as the radial or circumferential direction. The local average is moved throughout the entire data set and each pixel is compared to the local average. Points, which exceed the specified threshold above or below the local average, are denoted as defects. All the points, which exceed the specified threshold, are put together in a map of the surface showing the locations and amplitudes of all the defects. Contiguous points on the defect map are classified as a single defect. The aspect ratio (length to width ratio) is tested for each unique defect consisting of contiguous points. If the aspect ratio is long and thin then it is classified as a circumferential scratch, if not then a particle. The same process may be applied to the data from a circumferentially oriented head, but in this case, a long aspect ratio means a radial scratch and a short ratio a particle.

In an embodiment of the above-described functions and features for comparing and classifying defects, a computing device with a central processing unit (CPU) is used to process the scattered lighter image data collected from the disk surface. The CPU executes the above-described algorithm to process the images in order to compare and classify the defects. For example, the algorithm can be implemented as a computer program stored on a conventional storage device, in firmware or in hardware.

Figure 12:
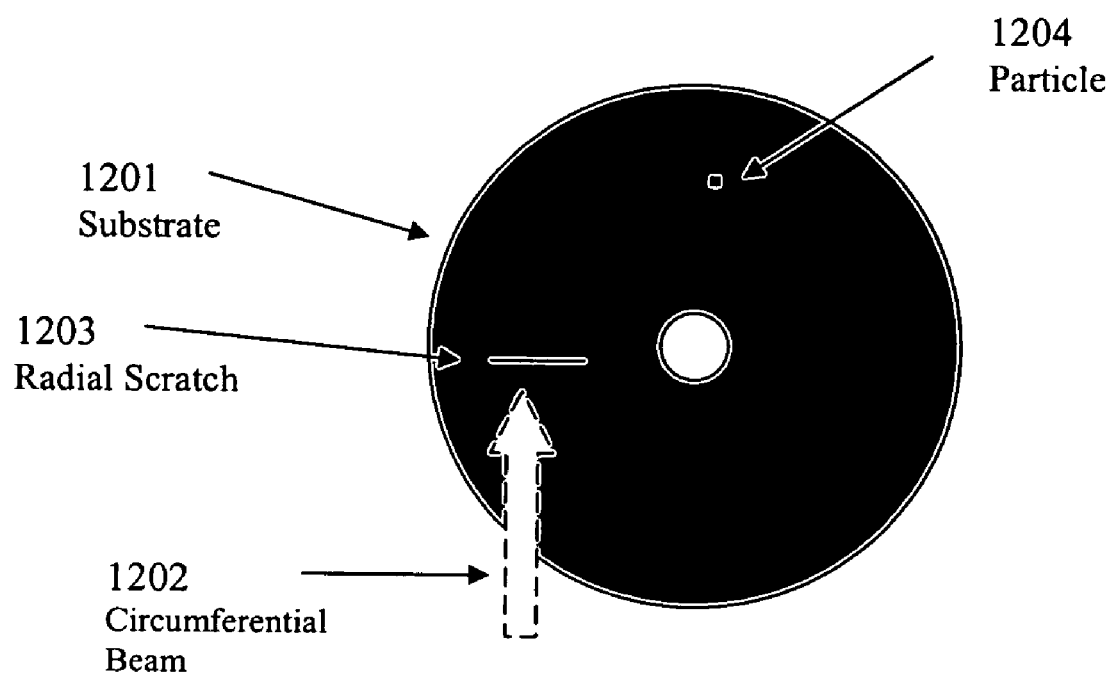
FIG. 12 is an illustration of a circumferential beam for detecting radial scratches and particles.

The case of detecting radial scratches or particles is shown in the embodiment shown in FIG. 12. In this case, the white light source in FIG. 8 is oriented above the disk or wafer 1201 in the circumferential direction 1202 and optimal scatter will come from radial scratches 1203 and particles 1204. Alternatively, a set of beams oriented in the circumferential direction as illustrated in FIG. 7 can be used, in which case it would not be necessary to rotate the disk. The circumferential texture 1103 (in FIG. 11) will have only minimal scatter in this embodiment. The advantage of this design is that it allows optimal measurement of particles and radial scratches since the circumferential texture has only minimal scatter light and hence does not add to the background "noise".

While the invention has been particularly shown and described with reference to a preferred embodiment and various alternate embodiments, it will be understood by persons skilled in the revelant art that various changes in form and details can be made therein without departing from the spirit and scope of the invention.

What is claimed is:

1. A method to detect a defect on a surface of an object, comprising:
   directing a first light beam along a first direction toward a first position on the surface of the object, where the first direction is a radial direction;
   directing a second light beam along a second direction toward the first position on the surface of the object, where the second direction is a circumferential direction:
   collecting a portion of the first light beam scattered from the surface of the object;
   collecting a portion of the second light beam scattered from the surface of the object; and
   identifying a defect on the surface of the object using an intensity characteristic of the portions of the first scattered light and the second scattered light collected from the surface.

2. The method of claim 1, wherein directing a first light beam along a first direction toward a first position on the surface of the object comprises directing the first light beam in a radial direction.

3. The method of claim 1, wherein directing a first light beam along a first direction toward a first position on the surface of the object comprises reflecting light from a light source from a parabolic mirror onto the surface of the object.

4. The method of claim 1, wherein collecting a portion of the light scattered from the first position on the object comprises focusing a portion of the reflected light onto a CCD camera.

5. The method of claim 4, wherein identifying a defect on the surface of the object using an intensity characteristic of the portion of the light collected comprises comparing an intensity characteristic of the portion of reflected light focused onto the CCD camera with a local average intensity characteristic.

6. The method of claim 1, further comprising:
   rotating the object about a central axis; and
   collecting a portion of the light scattered from the surface of the object while the object is rotating.

7. The method of claim 1 wherein:
   the first light beam is directed toward the surface of the object in a radial direction at a first point in time; and
   the second light beam is directed toward the surface of the object in a circumferential direction at a second point in time, different from the first point in time.

8. The method of claim 1 further comprising:
   determining a ratio of an intensity of scattered light reflected from the first light beam to an intensity of scattered light reflected from the second light beam; and
   using the ratio to classify a defect on the surface.

9. A system to detect a defect on a surface of an object, comprising:
   a first light source for directing a first light beam along a first direction toward a first position on the surface of the object, where the first direction is a radial direction;
   a second light source for directing a second light be am along a second direction toward the first position on the surface of the object, where the second direction is a circumferential direction;
   an optical assembly to collect portions of the first and second light scattered from the surface of the object;
   means for identifying a defect on the surface of the object using intensity characteristics of the portions of the first and second light collected from the surface.

10. The system of claim 9, wherein the first light source directs the first light beam in a radial direction.

11. The system of claim 9, wherein the first light source utilizes a parabolic mirror to direct light onto the surface of the object.

12. The system of claim 9, further comprising a Fresnel lens to focus a portion of the reflected light onto a CCD camera.

13. The system of claim 12, wherein the means for identifying a defect on the surface of the object comprises means for comparing an intensity characteristic of the portion of reflected light focused onto the CCD camera with a local average intensity characteristic.

14. The system of claim 9, further comprising:
   means for rotating the object about a central axis; and
   means for collecting a portion of the light scattered from the surface of the object while the object is rotating.

15. The system of claim 9 wherein:
   the first light beam is directed toward the surface of the object in a radial direction at a first point in time; and
   the second light beam is directed toward the surface of the object in a circumferential direction at a second point in time, different from the first point in time.

16. The system of claim 9 further comprising:
means for determining a ratio of an intensity of scattered light reflected from the first light beam to an intensity of scattered light reflected from the second light beam; and
means for using the ratio to classify a defect on the surface.

17. A method to detect a defect on a surface of an object, comprising:
directing a first plurality of light beams along a plurality of radial directions toward a first position on the surface of the object;
directing a second plurality of light beams along a plurality of circumferential directions toward the First position on the surface of the object:
collecting a portion of the first and second pluralities of light scattered from the surface of the object; and
identifying a defect on the surface of the object using intensity characteristics of the portions of the first and second pluralities of light collected from the surface.

18. The method of claim 17, wherein collecting a portion of the light scattered from the first position on the object comprises focusing a portion of the reflected light onto a CCD camera.

19. The method of claim 17, wherein identifying a defect on the surface of the object using an intensity characteristic of the portion of the, light collected comprises comparing an intensity characteristic of the portion of reflected light focused onto the CCD camera with a local average intensity characteristic.

20. The method of claim 5, wherein the local average intensity characteristic comprises averaging data for a specified length on the object along a specified orientation, wherein the specified orientation is either radial or circumferential.

21. The method of claim 8, wherein the first light beam is oriented circumferentially and the second light beam is oriented radially.

22. The method of claim 21, wherein using the ratio to classify a defect on the surface comprises using the ratio to discriminate between a first and second defect type, wherein the intensity of the first scatter light and intensity of the second scattered are within a known threshold of each other for the first defect type and outside a known threshold for the second defect type.

23. The method of claim 1 further comprising:
directing third through eighth beams along the first direction towards third through eighth positions on the surface of an object, wherein the first direction is within a know threshold of a radial or circumferential orientation.

24. The system of claim 13, wherein the local average intensity characteristic comprises averaging data for a specified length on the object along a specified orientation, wherein the specified orientation is either radial or circumferential.

25. The system of claim 16, wherein means for using the ratio to classify a defect on the surface comprises using the ratio to discriminate between a first and second defect type, wherein the intensity of the first scatter light and the intensity of the second scattered light are within a known threshold of each other for the first defect type and outside a known threshold for the second defect type.

26. The system of claim 9 further comprising:
a third through eighth light source for directing a third through eighth beam along the first direction towards third through eighth positions on the surface of the object, wherein the first direction is within a know threshold of a radial or circumferential orientation.

27. The method of claim 19, wherein the local average intensity characteristic comprises averaging data for a specified length on the object along a specified orientation, wherein the specified orientation is either radial or circumferential.

28. The method of claim 17, wherein the plurality of light beams comprises eight light beams.

* * * * *